United States Patent
Arensdorf

(10) Patent No.: US 7,828,759 B2
(45) Date of Patent: Nov. 9, 2010

(54) HEEL LOCK ANKLE SUPPORT

(76) Inventor: Stephen C. Arensdorf, 3711 Thunderbird Dr., Hays, KS (US) 67601

( * ) Notice: Subject to any disclaimer, the term of this patent is extended or adjusted under 35 U.S.C. 154(b) by 0 days.

(21) Appl. No.: 12/421,058

(22) Filed: Apr. 9, 2009

(65) Prior Publication Data

US 2009/0270784 A1 Oct. 29, 2009

Related U.S. Application Data

(63) Continuation of application No. 11/212,148, filed on Aug. 26, 2005, now abandoned.

(51) Int. Cl.
A61F 5/00 (2006.01)

(52) U.S. Cl. .................................................. 602/27

(58) Field of Classification Search .............. 128/882; 602/23, 26, 27, 28, 29, 60, 65, 66; 2/46, 2/61
See application file for complete search history.

(56) References Cited

U.S. PATENT DOCUMENTS

| | | | |
|---|---|---|---|
| 58,403 A | 10/1866 | Goodwin |
| 357,597 A | 2/1887 | Hazelton |
| 386,191 A | 7/1888 | Ferris |
| 491,123 A | 2/1893 | McClure |
| 891,977 A | 6/1908 | Bloch |
| 901,592 A | 10/1908 | Clegg |
| 1,295,297 A | 2/1919 | French |
| 1,374,177 A | 4/1921 | Barry |
| 1,374,669 A | 4/1921 | McClellan |
| 1,389,767 A | 9/1921 | Ludwig |
| 1,514,462 A | 11/1924 | Ritter |
| 1,573,212 A | 2/1926 | Whitley et al. |
| 1,587,508 A | 6/1926 | Coats |
| 1,602,454 A | 10/1926 | Riddell |
| 1,622,211 A | 3/1927 | Sheehan |
| 1,697,833 A | 1/1929 | Lane |
| 1,717,609 A | 6/1929 | Ludwig |
| 1,887,473 A | 11/1932 | Warner |
| 1,915,754 A | 6/1933 | O'Shea |
| 2,057,575 A | 10/1936 | Houghton |
| 2,165,081 A | 7/1939 | Wald |
| D123,025 S | 10/1940 | Colnes |
| 2,249,966 A | 7/1941 | Matthews |
| 2,251,018 A | 7/1941 | Lookabaugh |
| 2,266,886 A | 12/1941 | McCoy |
| 2,460,895 A | 2/1949 | Meany |
| 2,467,907 A | 4/1949 | Peckham |
| 2,539,170 A | 1/1951 | Waite et al. |

(Continued)

*Primary Examiner*—Patricia M Bianco
*Assistant Examiner*—Tarla R Patel
(74) *Attorney, Agent, or Firm*—Chase Law Firm, L.C.

(57) ABSTRACT

An ankle support has a tubular sock-like elastic sheath which, in use, is slipped over the foot and ankle of a wearer and extends upwardly over the lower leg, the sheath thereby having lateral and medial sides and a posterior end for receiving the heel of a wearer. Heel locks are provided by lateral and medial elastic locking straps secured to the sheath at a bottom portion of the posterior end of the sheath, and at a rear portion of the sheath (back of the heel) above the posterior end. The action of the two locking straps locks the heel of the wearer against lateral and medial movement. An elastic wrap on the sheath over the foot and ankle of the wearer overlies the lateral and medial portions of the locking straps to provide a lift to the heel.

4 Claims, 2 Drawing Sheets

U.S. PATENT DOCUMENTS

| | | |
|---|---|---|
| 2,570,497 A | 10/1951 | Senderowitz |
| 2,629,094 A | 2/1953 | Goldsmith |
| 2,774,073 A | 12/1956 | Herbener |
| 2,800,663 A | 7/1957 | Falk |
| 2,853,757 A | 9/1958 | Rave |
| 2,884,675 A | 5/1959 | Sternschuss |
| 2,930,046 A | 3/1960 | Sagner |
| 3,073,305 A | 1/1963 | Biggs, Jr. et al. |
| 3,146,461 A | 9/1964 | Kavanagh |
| 3,194,233 A | 7/1965 | Peckham |
| 3,237,257 A | 3/1966 | Forsberg |
| 3,295,530 A | 1/1967 | Mayer et al. |
| 3,310,053 A | 3/1967 | Greenwood |
| 3,350,719 A | 11/1967 | McClure, Jr. |
| 3,407,452 A | 10/1968 | Abert et al. |
| 3,431,560 A | 3/1969 | Austin |
| 3,463,147 A | 8/1969 | Stubbs |
| 3,506,000 A | 4/1970 | Baker |
| 3,515,142 A | 6/1970 | Black |
| 3,528,412 A | 9/1970 | McDavid |
| 3,581,741 A | 6/1971 | Rosman et al. |
| 3,584,622 A | 6/1971 | Domenico |
| 3,640,273 A | 2/1972 | Ray |
| 3,674,023 A | 7/1972 | Mann |
| 3,799,158 A | 3/1974 | Gardner |
| 3,885,252 A | 5/1975 | Nakajima |
| 3,909,847 A | 10/1975 | Holt et al. |
| 3,945,046 A | 3/1976 | Stromgren |
| 4,097,932 A | 7/1978 | Lacey |
| 4,136,226 A | 1/1979 | Gilman |
| 4,166,460 A | 9/1979 | Applegate |
| 4,179,826 A | 12/1979 | Davidson |
| 4,237,874 A | 12/1980 | Nelson |
| 4,249,524 A | 2/1981 | Anderson |
| 4,256,097 A | 3/1981 | Willis |
| 4,280,489 A | 7/1981 | Johnson, Jr. |
| 4,287,920 A | 9/1981 | Johnson, Jr. |
| 4,312,335 A | 1/1982 | Daniell, Jr. |
| 4,325,148 A | 4/1982 | Livernois |
| 4,367,733 A | 1/1983 | Stromgren |
| 4,370,754 A | 2/1983 | Donzis |
| 4,381,768 A | 5/1983 | Erichsen et al. |
| 4,428,080 A | 1/1984 | Takamatsu |
| 4,453,271 A | 6/1984 | Donzis |
| 4,455,686 A | 6/1984 | Zide |
| 4,462,115 A | 7/1984 | Carlson et al. |
| 4,479,269 A | 10/1984 | Balliet |
| 4,513,449 A | 4/1985 | Donzis |
| 4,628,945 A | 12/1986 | Johnson, Jr. |
| 4,670,945 A | 6/1987 | Banks |
| 4,691,697 A | 9/1987 | Arensdorf et al. |
| 4,700,407 A | 10/1987 | Mattila |
| 4,727,863 A | 3/1988 | Nelson |
| D301,566 S | 6/1989 | Heiberger |
| 4,844,058 A * | 7/1989 | Vogelbach .................. 602/27 |
| 4,878,274 A | 11/1989 | Patricy |
| 4,961,233 A | 10/1990 | Black |
| 4,962,768 A | 10/1990 | Stromgren et al. |
| 4,974,343 A | 12/1990 | Davidson |
| 5,007,416 A | 4/1991 | Burns et al. |
| 5,029,341 A | 7/1991 | Wingo, Jr. |
| 5,046,197 A | 9/1991 | Chernuchin et al. |
| 5,054,121 A | 10/1991 | Mitchell |
| 5,105,473 A | 4/1992 | Valtakari |
| 5,125,400 A | 6/1992 | Johnson, Jr. |
| 5,159,715 A | 11/1992 | Jurga et al. |
| 5,168,576 A | 12/1992 | Krent et al. |
| 5,172,494 A | 12/1992 | Davidson |
| 5,187,812 A | 2/1993 | Neuhalfen |
| D339,902 S | 10/1993 | Doherty |
| 5,259,096 A | 11/1993 | Grant |
| 5,361,410 A | 11/1994 | Sigl |
| 5,390,368 A | 2/1995 | Chang |
| D360,516 S | 7/1995 | Persinger |
| 5,487,187 A | 1/1996 | Zide et al. |
| 5,492,133 A | 2/1996 | McVicker |
| 5,493,736 A | 2/1996 | Allison |
| 5,536,246 A | 7/1996 | Saunders |
| 5,557,804 A | 9/1996 | Ovortrup et al. |
| 5,579,538 A | 12/1996 | Brunty |
| 5,636,380 A | 6/1997 | Schindler et al. |
| 5,676,641 A | 10/1997 | Arensdorf et al. |
| 5,781,935 A | 7/1998 | Bassett et al. |
| 5,792,714 A | 8/1998 | Schindler et al. |
| 5,840,397 A | 11/1998 | Landi et al. |
| 5,881,395 A | 3/1999 | Donzis |
| 5,974,592 A | 11/1999 | Tabrizi |
| 6,006,363 A | 12/1999 | Karlin |
| 6,023,789 A | 2/2000 | Wilson et al. |
| D423,188 S | 4/2000 | Raffali |
| 6,074,274 A | 6/2000 | Pyatt et al. |
| 6,098,209 A | 8/2000 | Bainbridge et al. |
| 6,145,132 A | 11/2000 | Towner |
| 6,161,222 A | 12/2000 | Strickland et al. |
| D445,724 S | 7/2001 | Kung |
| 6,336,220 B1 | 1/2002 | Sacks et al. |
| 6,363,538 B1 | 4/2002 | Davis |
| D456,995 S | 5/2002 | Baker |
| 6,401,250 B1 | 6/2002 | McNabb |
| 6,430,752 B1 | 8/2002 | Bay |
| D480,989 S | 10/2003 | Modolo |
| 6,629,945 B1 | 10/2003 | Stromgren |
| D486,093 S | 2/2004 | Tobergte |
| 6,845,522 B2 | 1/2005 | Béland |
| 6,880,269 B2 | 4/2005 | Falone et al. |
| 6,934,971 B2 | 8/2005 | Ide et al. |
| D525,765 S | 8/2006 | Arensdorf |
| D543,488 S | 5/2007 | Tobergte |
| 7,389,547 B1 | 6/2008 | Wiens |
| 7,506,384 B2 | 3/2009 | Ide et al. |
| 2004/0128748 A1 | 7/2004 | Monica |
| 2005/0229293 A1 | 10/2005 | Miller |

* cited by examiner

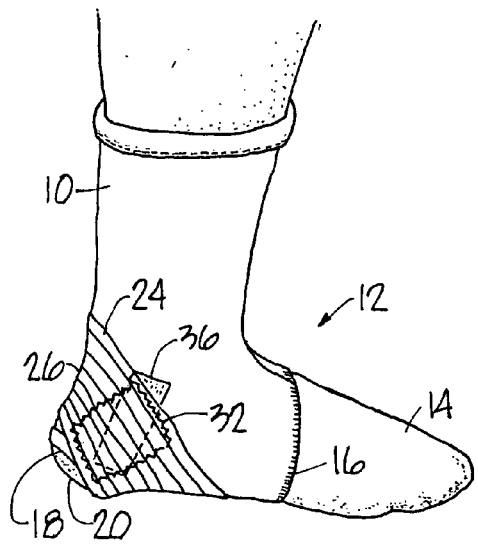
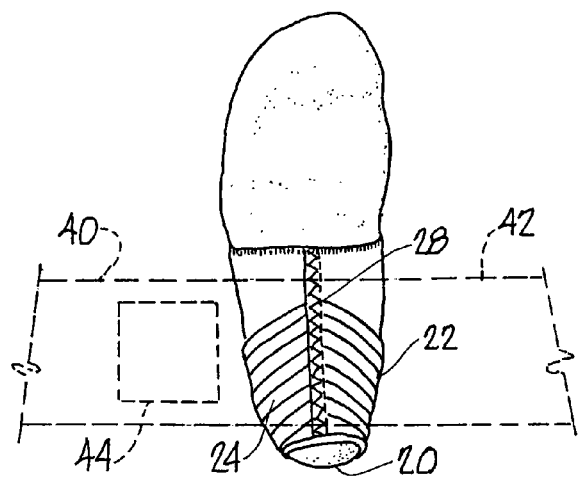
fig. 1
fig. 2
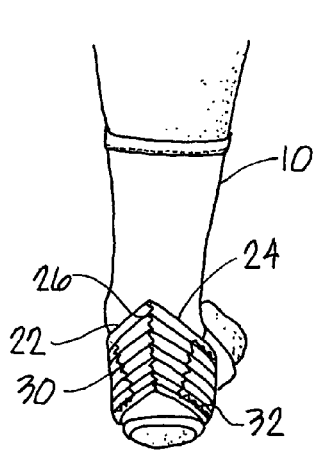
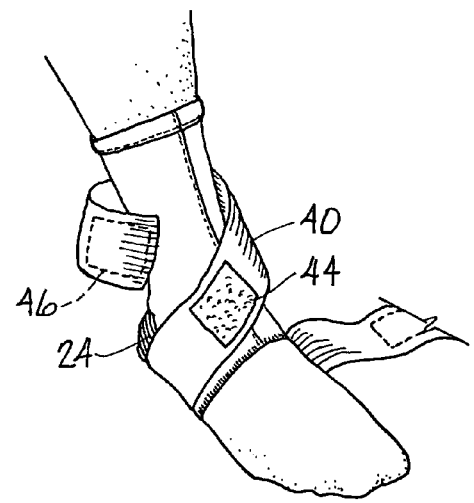
fig. 3
fig. 4

HEEL LOCK ANKLE SUPPORT

This application is a continuation of application Ser. No. 11/212,148, filed Aug. 26, 2005 now abandoned.

FIELD OF THE INVENTION

This invention relates to an ankle support for stabilizing the ankle complex of a wearer, particularly athletes and active persons, to provide protection from injury and post injury support.

BACKGROUND OF THE INVENTION

Ankle supports or wraps and taping of the ankle are commonly used to prevent or reduce the severity of debilitating ankle sprains. Athletes in both contact and noncontact sports are particularly susceptible to this injury. Methods of wrapping include the use of adhesive tape strapping, which is discarded after use, or reusable ankle wraps employing elastic material such as spandex or the like. Both taping of the ankle and reusable supports are applied to virtually immobilize the contact between the bones and the ligaments of the ankle region in order to prevent injurious pulling, stretching or tearing of these ligaments. Adhesive tapes, however, can be expensive to use, both because they are discarded after a single application and due to the time required by a coach or trainer to properly tape or supervise the taping of the ankle of an athlete.

A solution to this problem has been the utilization of reusable ankle wraps or supports of the general type as shown, for example, in U.S. Pat. Nos. 4,962,768 and 5,676,641. Although these supports have been successfully used by athletes and active individuals, they should be properly applied to the user in order to maximize effectiveness. If reusable supports are not applied in the recommended manner, effectiveness is reduced as compared to taping the ankle. Accordingly, it is desirable in reusable ankle supports to configure the support so that it can be readily applied as recommended and emulates a professionally taped ankle.

BRIEF DESCRIPTION OF THE INVENTION

In an embodiment of the present invention, an ankle support is provided that comprises a tubular sock-like elastic sheath which, in use, is slipped over the foot and ankle of a wearer and extends upwardly over the lower leg, the sheath thereby having lateral and medial sides and a posterior end for receiving the heel of a wearer. A first elastic locking strap on the lateral side of the sheath is extended to a stretched condition when the ankle support is worn and has one end secured to the sheath at a bottom portion of the posterior end of the sheath, and an opposite end secured to the sheath at a rear portion of the sheath (back of the heel) above the posterior end. A second elastic locking strap on the medial side of the sheath is extended to a stretched condition when the ankle support is worn, and has one end secured to the sheath at the bottom portion of the posterior end, and an opposite end thereof secured to the sheath at the rear portion behind the heel. The action of the two locking straps locks the heel of the wearer against lateral and medial movement. An elastic wrap on the sheath over the foot and ankle of the wearer overlies the lateral and medial portions of the locking straps, whereby the ankle support provides heel locks and a lift to the heel.

Other advantages of the invention will become apparent from the following description taken in connection with the accompanying drawings, wherein is set forth by way of illustration and example, an embodiment of the present invention.

BRIEF DESCRIPTION OF THE DRAWINGS

FIG. 1 is essentially an elevational view taken from the outside of the right foot showing the ankle support on the foot, but with the elastic wrap removed to show the position of the elastic locking strap on the lateral side of the foot.

FIG. 2 is a bottom plan view of the ankle support shown in FIG. 1 with the right foot reoriented and shows the ends of the two elastic locking straps secured to the sheath at the bottom of the foot adjacent the heel, the straps of the elastic wrap being shown fragmentarily and in broken lines before application to the foot.

FIG. 3 is a rear elevation of the support shown in FIG. 1, with the strap members of the elastic wrap removed for clarity.

FIGS. 4-7 show, in order, the steps of wrapping the elastic strap members around the ankle.

DETAILED DESCRIPTION

Figure 5:
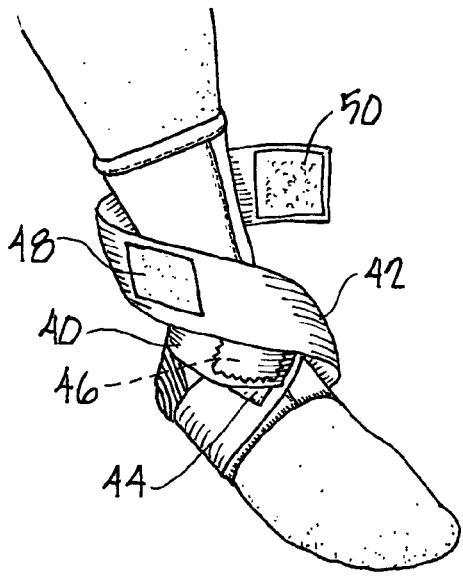

A tubular, sock-like elastic sheath 10 receives the foot 12 and lower leg of a wearer as is clear in the drawings, the sheath 10 being slipped over the foot 12 which preferably has an athletic sock 14 thereon. The sheath 10 has a front opening 16 from which the toes and part of the foot 12 extend, and a heel opening 18 at the posterior end of the sheath 10 through which the heel 20 of the foot protrudes. The sheath 10 is made from an elastic fabric such as spandex or the like, and is sized to have an unstretched diameter somewhat less than the wearer's leg so that the fabric is stretched as it is pulled over the foot 12 into position. The preferred material has four-way stretchability, meaning that it has resilience in directions up and down the leg as well as circumferentially. This holds the sheath 10 in place and also imparts some support to the ankle region.

An elastic locking strap 22 overlies the medial side of the heel, and an elastic locking strap 24 overlies the lateral side of the heel. Each of the locking straps 22 and 24 is permanently attached to the sheath 10 by a vertically extending line of stitching 26 at the back of the heel (FIG. 3) and a line of stitching 28 on the bottom of the sheath 10 extending from front to rear beneath the heel (FIG. 2). Accordingly, the posterior ends of the straps 22 and 24 are secured to the sheath 10 at the back of the heel or posterior end of the sheath 10, and the lower ends are secured to the sheath 10 at the rear portion thereof beneath the heel and forwardly of the heel opening 20. Thus, angled elastic straps 22 and 24 are presented which, as will be discussed below, present heel locks that provide stabilization to the ankle complex.

In addition to the stitching 26 and 28, Velcro® fasteners 30 and 32 are also provided on locking straps 22 and 24, respectively, to secure the central portions of the locking straps in place on the sheath 10 as they extend downwardly, outwardly and under the heel as may be appreciated from a comparison of FIGS. 1, 2 and 3. Mating Velcro® fasteners are sewn to the sheath 10 as illustrated at 36 in FIG. 1 for the lateral side. Therefore, the elastic locking straps 22 and 24 are maintained in the positions illustrated in the figures as the ankle support is removed and reinstalled and are thus held in the positions illustrated over the medial and lateral sides of the heel.

Figure 6:
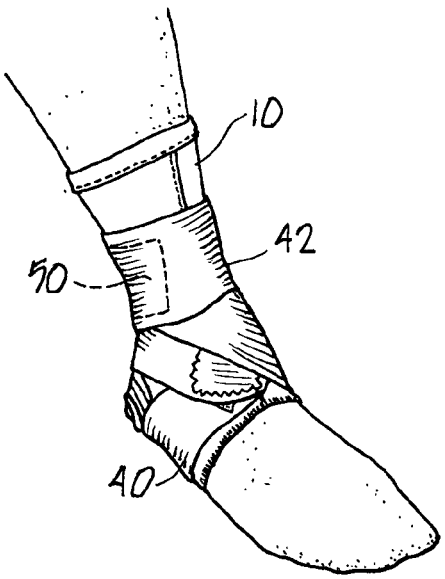
Figure 7:
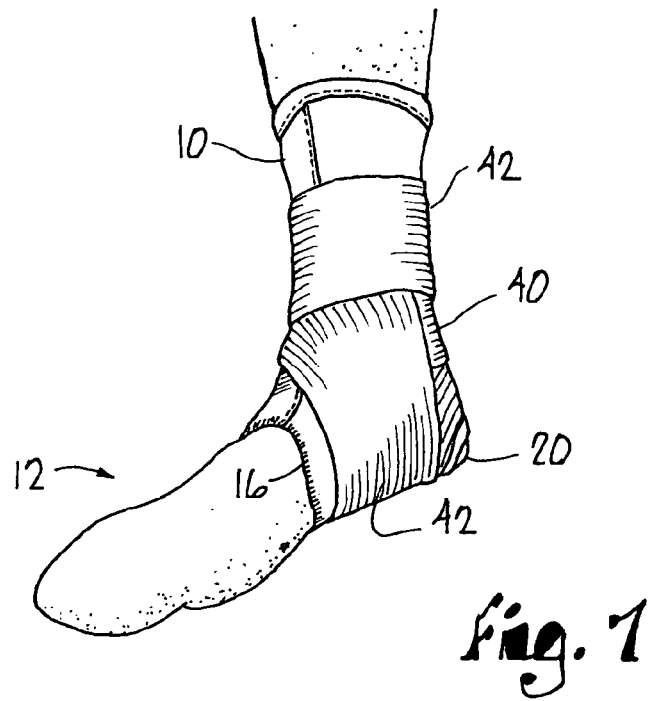

Supplementing the locking straps 22 and 24, a pair of elongated elastic strap members 40 and 42 are provided and apply a wrap as illustrated in the sequential views 4-7. The lower end portions of the strap members 40 and 42 are seen in phantom lines in FIG. 2 where it may be appreciated that the terminal ends thereof are held by the line of stitching 28 that also secures the locking straps 22 and 24. Preferably, the member 40 that extends laterally from the bottom of the foot is somewhat shorter than the member 42 that extends medially. The sequence of the wrap begins (FIG. 4) by drawing member 40 across the tibia and to the rear thereof, and then across the fibula to the front where Velcro® fasteners 44 and 46 on the member 40 mate (FIG. 5). Strap member 42 is then drawn into position as shown in FIGS. 5-7, above and partially overlapping member 40 by wrapping in the opposite direction as illustrated. In its final position as seen in FIGS. 6 and 7, member 42 is secured by mating Velcro® fasteners 48 intermediate the ends of member 42, and 50 at the end thereof.

In use, the sheath 10 is slipped over the ankle of the wearer to the position illustrated where the heel 20 of the wearer protrudes from the heel opening 18. The locking straps 22 and 24 are thus positioned in an angled orientation extending from the bottom of the foot upwardly and rearwardly to the line of stitching 26. The angled straps 22 and 24 comprise an elastic material having a two-way stretch, i.e., a lengthwise stretch and elongation as the support is pulled over the foot into position. As the wearer pulls the sheath 10 onto his or her foot and stretches the material to its final position shown, for example, in FIGS. 1-3, each of the elastic straps 22, 24 extends to its limit of elasticity thus creating fixed heel locks on the medial and lateral sides of the foot. It may be appreciated, therefore, that the length of each of the straps 22, 24 from the bottom line of stitching 28 to the substantially vertically extending line of stitching 26 at the back of the heel is selected in accordance with the particular material used to provide a maximum stretch in the fully installed position of the support shown in FIGS. 1-3. In this manner, the heel locks stabilize the heel complex to control severe inversion and eversion that can cause an ankle sprain.

The two strap members 40 and 42 supplement the heel locks and are also longitudinally stretchable to a maximum extension. The shorter strap member 40 is wrapped low around the ankle complex and the longer strap member 42 is then wrapped in the opposite direction somewhat higher on the upper part of the ankle as is apparent in FIGS. 5-7. The strap configuration is similar to the final process in taping an ankle and creates a lift to the heel of the wearer. This assists in bringing the wearer up on the ball of the foot for better rotation, again helping to reduce the chances of an ankle sprain. Accordingly, the ankle support provides the combination of fixed heel locks and a heel lift in a support that is easy to put on quickly and correctly and is reusable.

It is to be understood that while certain forms of this invention have been illustrated and described, it is not limited thereto, except insofar as such limitations are included in the following claims.

Having thus described the invention, what is claimed as new and desired to be secured by Letters Patent is as follows:

1. An ankle support comprising:
   a tubular sock-like elastic sheath adapted to be slipped over a foot and ankle of a wearer and, when worn, to extend upwardly therefrom over the lower leg, said sheath having lateral and medial sides and having a posterior end for receiving the heel of a wearer,
   a first elastic locking strap on said lateral side extended to a fully stretched condition when the ankle support is worn, and having one end secured to said sheath at a bottom portion of said posterior end under the foot, and an opposite end secured to said sheath along an upwardly extending line of attachment to the sheath at the back of the heel above said posterior end of the sheath, said line of attachment comprising an upwardly extending line of stitching,
   a second elastic locking strap on said medial side extended to a fully stretched condition when the ankle support is worn, and having one end thereof secured to said sheath at said bottom portion of said posterior end under the foot, and an opposite end thereof secured to said sheath at said line of attachment to the sheath at the back of the heel, whereby said locking straps lock the heel of a wearer against lateral and medial movement, and
   an elastic wrap on said sheath over the foot and ankle of the wearer and overlying lateral and medial portions of said locking straps, whereby to provide heel locks and a lift to the heel of the wearer of the support.

2. The ankle support as claimed in claim 1, wherein said elastic wrap includes a pair of elongated elastic strap members each having a first and second ends, said first end of each strap member being secured to said sheath at said bottom portion, said strap members in use being wrapped around said sheath in opposite directions over the ankle of the wearer into operative positions, and fasteners associated with the second ends of the strap members for securing the same in said operative positions.

3. An ankle support comprising:
   a tubular sock-like elastic sheath adapted to be slipped over a foot and ankle of a wearer and, when worn, to extend upwardly therefrom over the lower leg, said sheath having lateral and medial sides and a heel opening for receiving the heel of a wearer,
   a first elastic locking strap on said lateral side extended to a stretched condition when the ankle support is worn, and having one end secured to said sheath at a bottom portion thereof under the foot and adjacent said heel opening, and means securing an opposite end of said first strap to said sheath above said heel opening along an upwardly extending line of attachment at the back of the heel, said line of attachment comprising an upwardly extending line of stitching, and
   a second elastic locking strap on said medial side extended to a fully stretched condition when the ankle support is worn, and having one end thereof secured to said sheath at said bottom portion, and means securing an opposite end thereof to said sheath at said line of attachment above said heel opening, whereby said locking straps lock the heel of a wearer against lateral and medial movement.

4. A method of stabilizing the ankle complex of a person comprising the steps of:
   providing a tubular sock-like elastic sheath adapted to be slipped over a foot and ankle of a wearer and, when worn, to extend upwardly therefrom over the lower leg, said sheath having lateral and medial sides and a heel opening for receiving the heel of a wearer,
   providing a first elastic locking strap on said lateral side extended to a stretched condition when the ankle support is worn, and having one end secured to said sheath at a bottom portion of said posterior end under the foot, and an opposite end secured to said sheath along an upwardly extending line of attachment to the sheath at the back of the heel above said posterior end of the sheath, said line of attachment comprising an upwardly extending line of stitching,
   providing a second elastic locking strap on said medial side extended to a stretched condition when the ankle support is worn, and having one end thereof secured to said sheath at said bottom portion, and an opposite end thereof secured to said sheath at said line of attachment, whereby said locking straps lock the heel of a wearer against lateral and medial movement, and
   providing an elastic wrap on said sheath over the foot and ankle of the wearer and overlying lateral and medial portions of said locking straps, whereby to provide heel locks and a lift to the heel of the wearer of the support.

* * * * *